US00PP14831P2

(12) United States Plant Patent
Yomo

(10) Patent No.: US PP14,831 P2
(45) Date of Patent: May 25, 2004

(54) VERBENA PLANT NAMED 'SUNMAREF TPPW'

(50) Latin Name: *Verbena hybrida*
Varietal Denomination: Sunmaref TPPW

(75) Inventor: Yasunori Yomo, Kawasaki (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/327,943

(22) Filed: Dec. 26, 2002

(51) Int. Cl.[7] ..... A01H 5/00
(52) U.S. Cl. ..... Plt./308
(58) Field of Search ..... Plt./308

(56) References Cited

U.S. PATENT DOCUMENTS

| | | | |
|---|---|---|---|
| PP8,995 | P | 11/1994 | Tachibana et al. |
| PP9,014 | P | 12/1994 | Tachibana et al. |
| PP9,059 | P | 2/1995 | Tachibana et al. |
| PP9,085 | P | 3/1995 | Tachibana et al. |
| PP9,121 | P | 4/1995 | Tachibana et al. |
| PP9,411 | P | 12/1995 | Tachibana et al. |
| PP10,311 | P | 3/1998 | Tachibana |
| PP10,705 | P | 11/1998 | Tachibana |
| PP10,743 | P | 1/1999 | Nagase |
| PP10,755 | P | 1/1999 | Nagase |
| PP10,801 | P | 2/1999 | Nagase |
| PP11,037 | P | 8/1999 | Yomo et al. |
| PP11,104 | P | 10/1999 | Yomo et al. |
| PP11,113 | P | 11/1999 | Yomo et al. |
| PP11,120 | P | 11/1999 | Yomo et al. |
| PP11,130 | P | 11/1999 | Yomo et al. |

*Primary Examiner*—Anne Marie Grunberg
*Assistant Examiner*—Susan B. McCormick
(74) *Attorney, Agent, or Firm*—Burns, Doane, Swecker & Mathis, L.L.P.

(57) ABSTRACT

A new Verbena plant is provided having a spreading growth habit and long stems. The plant displays abundant branching and abundantly forms flowers in a spike with a great profustion of blooms. The blooming period is April to November and flowering duration is long with the entire plant remaining in bloom for a considerable period of time. The flower size is medium and the flower petal coloration is white. The plant displays high tolerances to cold, drought, rain and heat, and high resistances to pests and diseases, particularly with respect to powdery mildew.

2 Drawing Sheets

Botanical/commercial classification: *Verbena hybrida*/ Verbena Plant.
Varietal denomination: cv. 'Sunmaref TPPW'.

BACKGROUND OF THE VARIETY

Verbena is a very popular plant and is used for flower bedding and potting in the summer season. There are only a few varieties of the Verbena plants which have a spreading growth habit, abundant branching, and form a large number of flowers in a spike and which have high resistances to rain, heat, cold, and diseases. Accordingly, this invention was aimed at obtaining a new Verbena variety having a spreading growth habit, abundant branching, the formation of a large number of flowers in a spike that manifest high tolerances to heat, rain, drought and cold, and high resistances to diseases and pests.

The new variety of Verbena plant according to this invention originated from crossing as female parent the 'Long Run White' variety (non-patented in the United States) and as male parent the 'V-Tenera White' variety (non-patented in the United States).

Initially, 20 seedlings were obtained in 1988 from this crossing. Nine seedlings were selected for further observation in view of their spreading growth habit and flower color. From among these seedlings one seedling was finally selected in view of its long flowering duration. This seedling was propagated by the use of cuttings and was grown and evaluated while present in pots and flower beds. The botanical characteristics of the seedling were examined while using similar varieties 'Sunmaref TP-W' U.S. Plant Pat. No. 9,059) and 'Sunmaref TP-P' (U.S. Plant Pat. No. 9,014) for comparison from May to November of 1999. As the result, it was concluded that this new Verbena plant is distinguishable from any other variety, whose existence is known to me, and is uniform and stable in its characteristics. This new variety of Verbena plant was named 'Sunmaref TPPW'.

In the following description, the color-coding is in accordance with The R.H.S. Colour Chart of The Royal Horticultural Society, London, England. A color chart based on The Japan Color Standard for Horticultural Plant (J.H.S. Color Chart) is also added for reference.

The 'Long Run White' variety used as female parent, was bred by the Takii Seed Corp, of Japan and is commercially available. The main botanical characteristics of the 'Long Run White' variety are as follows:

Plant:
*Growth habit.*—Semi-erect.
*Plant width.*—Approximately 25–30 cm.
*Plant height.*—Approximately 20–25 cm.
Stem:
*Diameter.*—Approximately 2.0–3.3 mm.
*Anthocyanin pigmentation.*—Absent.
*Branching.*—Medium.
*Subterranean stem.*—Absent.
*Pubescence.*—Sparse.
*Length of internode.*—Approximately 3.0–3.5 cm.
Leaf:
*Phyllotaxis.*—Opposite.
*Shade of blade.*—Cordate.

*Length.*—Approximately 1.7–2.4 cm.
*Width.*—Approximately 1.5–2.1 cm.
*Depth of incision.*—Deep.
*Color.*—Dark green (R.H.S. 137A, J.H.S. 3707).
*Pubescence.*—Sparse.

Flower:
*Facing direction.*—Upward.
*Outward curvature of petal.*—Curved.
*Diameter.*—Approximately 1.0–1.5 cm.
*Height.*—Approximately 13–15 mm.
*Color.*—White (R.H.S. 155C, J.H.S. 01).
*Color intensity.*—Absent.
*Overlapping of petals.*—Open.
*Spike.*—Approximately 25–30 mm in length; and approximately 30–35 mm in diameter.
*Calyx.*—Approximately 0.5–1.0 cm in length.
*Anthocyanin pigmentation of calyx limb.*—Present.
*Peduncle.*—Approximately 1.7–1.8 mm in thickness; and approximately 4.0–6.0 cm in length.
*Number of flowers.*—Few (approximately 7–11).
*Reproductive organs.*—1 pistil and 5 stamens.
*Flower fragrance.*—Absent.
*Flowering duration.*—Medium.

Physiological and ecological characteristics: Moderate tolerances to heat, cold, and pests and low resistance to diseases.

The Verbena plant named 'V-Tenera White' used as male parent white-flowering, is native to Brazil, and is not commercially available. This parent plant is presently maintained at the Omi R & D Center of Suntory Flowers Ltd., located at 863-1, Aza-Iketani, Omori-cho, Yokaichi-shi, Shiga-ken, Japan. The main botanical characteristics of this male parent are as follows:

Plant:
*Growth habit.*—Slightly erect and spreading.
*Plant width.*—Approximately 65–100 cm.
*Plant height.*—Approximately 5–8 cm.

Stem:
*Diameter.*—Approximately 1.0–2.0 mm.
*Anthocyanin pigmentation.*—Present.
*Branching.*—Medium.
*Subterranean stem.*—Absent.
*Pubescence.*—Medium.
*Length of internode.*—Approximately 2.0–5.0 cm.

Leaf:
*Phyllotaxis.*—Opposite.
*Shape of blade.*—Narrow lanceolate.
*Length.*—Approximately 2.0–4.0 cm.
*Width.*—Approximately 1.0–2.0 cm.
*Depth of incision.*—Deep.
*Color.*—Dark green (R.H.S. 143A, J.H.S. 3707).
*Pubescence.*—Sparse.

Flower:
*Facing direction.*—Upward.
*Outward curvature of petal.*—Slightly curved.
*Diameter.*—Approximately 1.3–1.5 cm.
*Height.*—Approximately 13–15 mm.
*Color.*—White (R.H.S. 155C, J.H.S. 01).
*Color intensity.*—Absent.
*Overlapping of petals.*—Separate.
*Spike.*—Approximately 20–25 mm in length; and approximately 30–40 mm in diameter.
*Calyx.*—Approximately 1.0 cm in length.
*Anthocyanin pigmentation of calyx limb.*—Present.
*Peduncle.*—Approximately 1–2 mm in thickness; and approximately 4.0–5.0 cm in length.
*Number of flowers.*—Plentiful (approximately 13–15).
*Reproductive organs.*—1 pistil and 5 stamens.
*Flower fragrance.*—Absent.
*Flowering duration.*—Short.

Physiological and ecological characteristics: High resistances to diseases and pests, high tolerance to heat, and moderate tolerance to cold.

This new variety of Verbena plant 'Sunmaref TPPW' has been asexually reproduced by the use of cuttings at the Omi R&D Center, Flower Division, Suntory Ltd, 863-1 Aza-Iketani Omori-cho Yokaichi-shi, Shiga-ken, Japan, and the homogeneity and stability thereof were confirmed. The instant plant retains its distinctive characteristics and reproduces true to type in successive generations.

SUMMARY OF THE VARIETY

This new variety of Verbena plant has a spreading growth habit and short stems. The plant displays abundant branching, and forms flowers in a spike with a great profusion of blooms. The blooming period commonly is April to November and the flowering duration is long. The entire plant remains in bloom for a considerable period of time. The flower size is large and the flower petal coloration is white. The plant has high tolerances to cold, heat, rain and drought, and high resistances to pests and diseases, particularly powdery mildew. Once cuttings of the new variety are placed, roots are well developed in approximately twenty days.

BRIEF DESCRIPTION OF THE PHOTOGRAPHS

DESCRIPTION OF THE VARIETY

Figure 1:
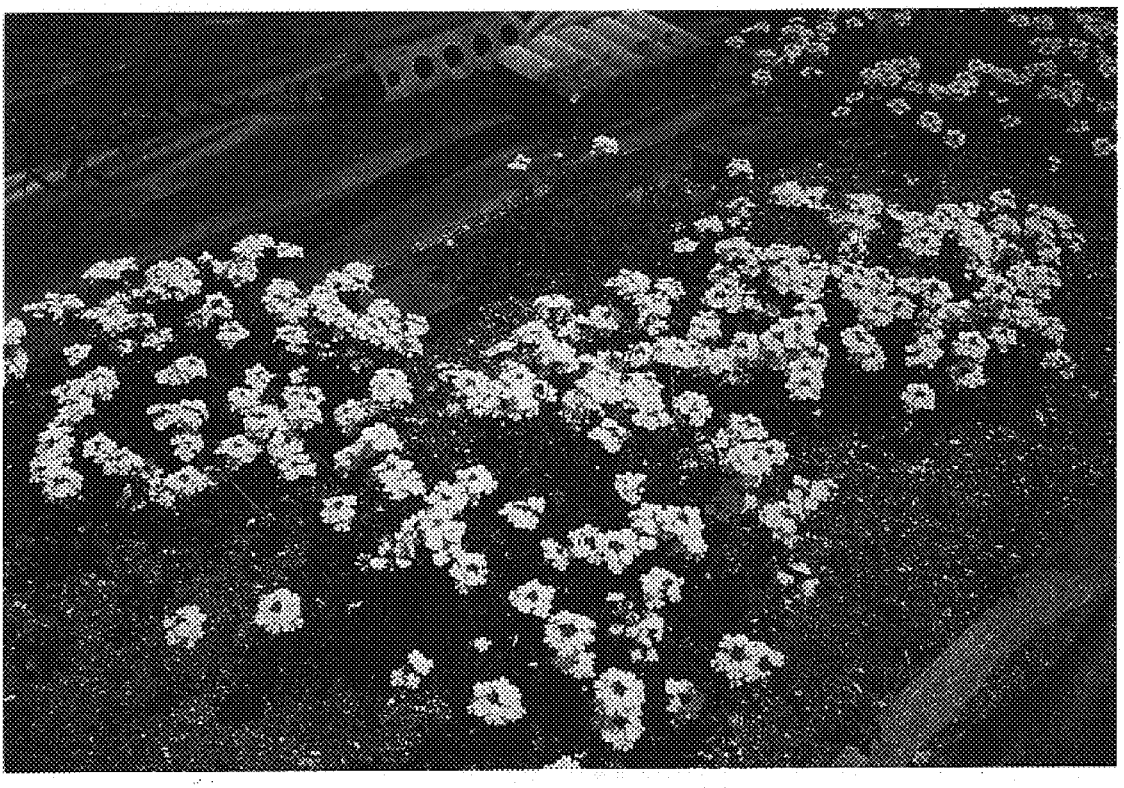
FIG. 1 shows the new variety of Verbena plant 'Sunmaref TPPW' when growing in a flower bed.
Figure 2:
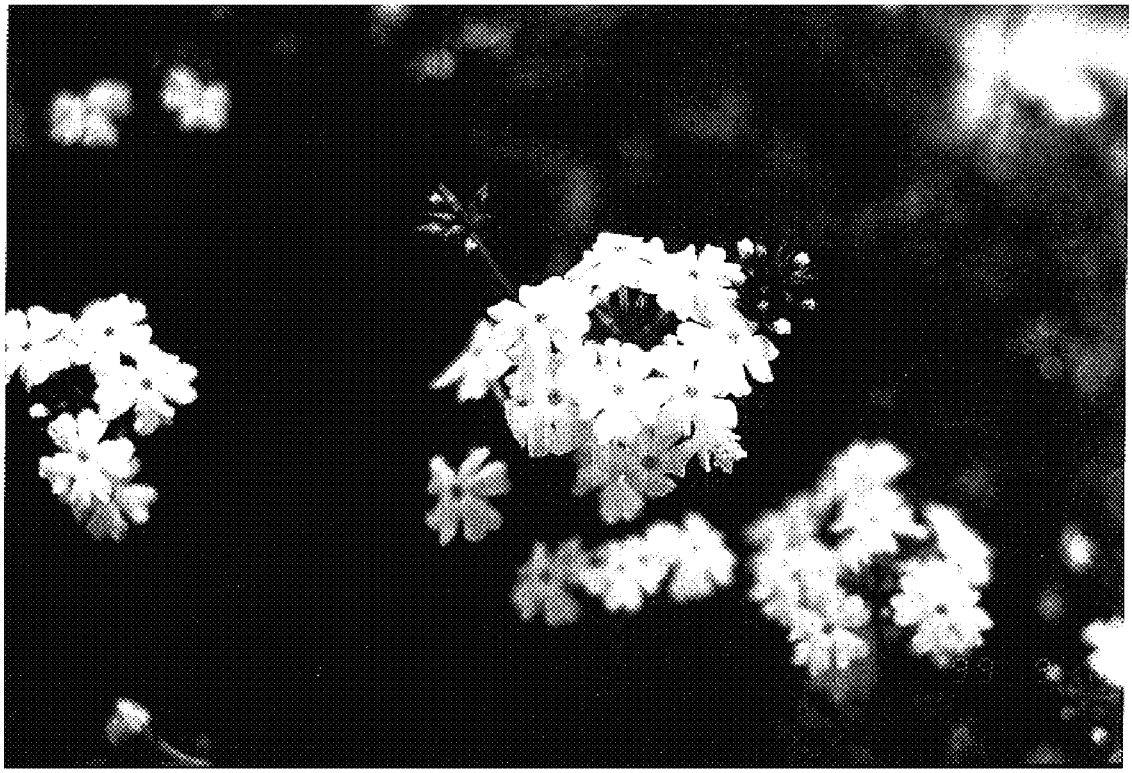
FIG. 2 shows a closer view of the flowers of the new variety of Verbena plant 'Sunmaref TPPW'.

The botanical characteristics of the new and distinct variety of Verbena plant, 'Sunmaref TPPW' are as follows:

Plant:
*Growth habit.*—Spreading.
*Plant width.*—Approximately 50–60 cm.
*Plant height.*—Approximately 18–23 cm.
*Growth.*—Very vigorous with abundant branching and a great profusion of blooms with the entire plant remaining in bloom for considerable period of time.

Stem:
*Diameter.*—Approximately 1.5–2.0 mm.
*Anthocyanin pigmentation.*—Present.
*Branching.*—Abundant.
*Subterranean stem.*—Absent.
*Pubescence.*—Rough.
*Length of internode.*—Short, approximately 2.0–3.0 cm.

Leaf:
*Phyllotaxis.*—Opposite.
*Shape of blade.*—Cordate
*Length.*—Approximately 1.5–2.0 cm.
*Width.*—Approximately 1.5–2.0 cm.
*Depth of incision.*—Deep.

*Color.*—Dark green (R.H.S. 139A, J.H.S. 3708) on the upper surface and lighter green (R.H.S. 138B) on the under surface.

*Vein color.*—R.H.S. 139C on the upper surface and 139D on the under surface.

*Petiole length.*—Approximately 5 mm.

*Petiole diameter.*—Approximately 1 mm.

*Petiole color.*—R.H.S. 137D.

*Pubescence.*—Rough.

Flower:

*Facing direction.*—Upward.

*Outward curvature of petal.*—Curved.

*Diameter.*—Approximately 1.3–1.6 cm.

*Height.*—Approximately 12–14 mm.

*Petal color.*—White (R.H.S. 155B, J.H.S. 01) on both surfaces.

*Flower tube color.*—R.H.S. 192B.

*Color intensity.*—Absent.

*Arrangement of petals.*—Overlapping

*Spike.*—Approximately 30–50 mm in length; and approximately 30–40 mm in diameter.

*Flower tube.*—Approximately 0.5 to 1.0 cm in length.

*Petal length.*—Approximately 3 to 5 mm.

*Petal width.*—Approximately 3 to 4 mm.

*Petal apex.*—Indented.

*Calyx length.*—Approximately 0.5–1.0 cm.

*Calyx color.*—R.H.S. 137D.

*Anthocyanin pigmentation of calyx limb.*—Present.

*Peduncle.*—Approximately 1.0 to 2.0 mm in diameter, and approximately 3.0–4.0 cm in length.

*Number of flowers.*—Medium (approximately 7–12) in the form of an umbel.

*Reproductive organs.*—1 pistil and 5 stamens.

*Flower fragrance.*—Absent.

*Flowering duration.*—Long.

*Seeds.*—Commonly approximately four seeds are formed per flower which are approximately 3 to 5 mm in diameter, and R.H.S. 165A in coloration.

Physiological and ecological characteristics: High resistances to diseases and pests, particularly powdery mildew. High tolerances to heat, cold, rain and drought.

This new variety of Verbena plant is most suitable for growing in flower beds and pots, particularly in planters, and is further is excellent for use as a ground cover.

Plants of the new 'Sunmaref TPPW' variety have not been observed under all possible environmental conditions to date. Accordingly, it is possible that the phenotypic expression may vary somewhat with changes in light intensity and duration, cultural practices, and other environmental conditions.

I claim:

1. A new and distinct Verbena plant, substantially as herein illustrated and described, characterized particularly as to novelty by (A) a spreading growth habit with long stems, (B) abundant branching and the formation of a large number of flowers in a spike with a great profusion of blooms and a long flowering duration, with the entire plant remaining in bloom for a considerable period of time, (C) the formation of white-petaled flowers. and (D) high tolerances to rain, heat, drought, cold, and high resistances to diseases and pests, particularly with respect to powdery mildew.

* * * * *